(12) United States Patent
Killam

(10) Patent No.: US 6,500,808 B2
(45) Date of Patent: Dec. 31, 2002

(54) ANTI-VIRAL COMPOSITION

(75) Inventor: Harold Killam, Melrose, MA (US)

(73) Assignee: Alpha Solar Corporation, Melrose, MA (US)

( * ) Notice: Subject to any disclaimer, the term of this patent is extended or adjusted under 35 U.S.C. 154(b) by 0 days.

(21) Appl. No.: 10/039,968

(22) Filed: Oct. 19, 2001

(65) Prior Publication Data

US 2002/0099022 A1 Jul. 25, 2002

Related U.S. Application Data

(62) Division of application No. 09/608,029, filed on Jun. 30, 2000.

(51) Int. Cl.[7] .................. A01N 43/04; A01N 61/00; A61K 31/715; A61K 38/00; C07H 19/00
(52) U.S. Cl. .................. 514/53; 514/1; 514/44; 530/300; 530/350; 536/22.1; 536/23.1
(58) Field of Search ................. 514/1, 44, 53; 530/300, 350; 536/22.1, 23.1

(56) References Cited

U.S. PATENT DOCUMENTS 5,681,815 A 10/1997 Fan et al. ............. 514/12
6,046,228 A  4/2000 Rice et al. ............ 514/441

OTHER PUBLICATIONS

International Search Report (PCT/US01/20579).

Primary Examiner—Jezia Riley
(74) Attorney, Agent, or Firm—Palmer & Dodge, LLP; Kathleen M. Williams; Mark J. FitzGerald

(57) ABSTRACT

The invention relates to zinc-containing antiviral compositions and methods of treating viral infections. More specifically, the invention provides compositions and methods useful for ameliorating the symptoms of individuals suffering from infection with a broad range of viruses. Examples of viruses against which the compounds of the invention are active include rhinoviruses, varicella zoster, immunodeficiency viruses, including HIV.

8 Claims, 3 Drawing Sheets

COMPOSITION A

L-Asp      Structure 1      Structure 2      D-Asp

Structure 3

Structure 4

COMPOSITION B

L-Asp

Structure 1

Structure 3

COMPOSITION C

Structure 2

Structure 4

ANTI-VIRAL COMPOSITION

This application is a divisional of U.S. Utility application Ser. No. 09/608,029, filed Jun. 30, 2000, which is hereby incorporated herein by reference, in its entirety, including drawings.

FIELD OF THE INVENTION

The invention relates to compositions for the treatment or prevention of viral infection. The invention also relates to compositions for the treatment of tumors.

BACKGROUND

Illnesses resulting from viral infection remain as a major problem to be addressed by modern medicine. To date, there is no 100% effective treatment for infection with any known virus. Recently there has been progress towards treatment of several viral diseases, but these treatments are largely directed at specific viruses or classes of viruses. For example, protease inhibitors targeting the virally-encoded human immunodeficiency virus (HIV) protease have been effective against some strains of HIV, and have been responsible, when used in combination with other anti-viral agents, for a decline in HIV-related deaths in the United States. However, the protease inhibitors are specific for specific viruses or classes of viruses, and are not useful for the treatment of viruses outside of those classes. In addition, there is evidence that strains resistant to these new agents are evolving.

It is noted that the virus-specific agents currently being used in developed countries are very expensive, being beyond the means of a great number of infected individuals throughout the world. In addition, the dosage regimens are complex and demand careful attention by physicians and the infected individuals.

Because viruses co-opt the host's own normal intracellular metabolic processes for their reproductive needs, a major difficulty in the design of antiviral agents is to make agents that target the virus without toxicity to the host organism.

There is a need in the art for antiviral agents that are effective against a broad spectrum of viruses, relatively non-toxic, inexpensive to produce, and simple to administer.

Many of the same problems plaguing those attempting to develop antiviral therapies are faced by those wishing to cure cancer. Transformed cancer cells share the same cellular metabolic processes as non-transformed cells, differing primarily in a loss of normal growth control. Therefore, it has been difficult to develop treatment strategies that are effective against tumor cells without significant toxicity to non-tumor cells. There is a need in the art for effective anti-tumor therapies that minimize the toxicity to non-transformed cells and tissues.

SUMMARY OF THE INVENTION

The invention relates to methods and compositions for treating the symptoms of viral infection and for reducing the size or cellular load of a tumor.

More specifically, the invention encompasses a composition comprising the chemical compounds of Structure Nos. 1–4 and analogs thereof with antiviral activity. The invention also encompasses a composition consisting essentially of any one or a combination of the chemical compounds of Structure Nos. 1–4. The invention also encompasses a composition comprising at least 10%, 20%, 50%, 75%, 90%, 95% or 99% of any one or a combination of structures 1–4 by weight. Structures 1 and 2 are chiral, as are structures 3 and 4. A composition of the invention may have relative amounts of (Structures 1 and 2): (Structures 3 and 4) in proportions ranging from 1:100, 1:10, 1:1, 10:1, or even 100:1.

The invention also encompasses an antiviral composition comprising a mixture of zinc oxide, aspartic acid, and high fructose corn syrup.

In one embodiment, the composition comprising a mixture of zinc oxide, aspartic acid, and high fructose corn syrup comprises one mass unit of zinc oxide, about 2.5 mass units of aspartic acid, and about 64.5 mass units of high fructose corn syrup.

The invention further encompasses an antiviral composition consisting essentially of a mixture of zinc oxide, aspartic acid and high fructose corn syrup.

In a preferred embodiment, the high fructose corn syrup has the following characteristics: a) about 77% solids and about 23% moisture; and b) a carbohydrate composition as follows: about 55% fructose; about 41% dextrose; the remainder being higher saccharides. In another embodiment, pure fructose (i.e., a composition consisting essentially of fructose), or a composition comprising about 96% fructose and 4% higher polysaccharides, is used in the preparation of an antiviral composition of the invention.

The invention further encompasses a method of making an antiviral or antitumor composition, such method comprising the steps of: a) combining zinc oxide, aspartic acid and high fructose corn syrup to form a mixture; b) heating the mixture until visible insoluble material is absent; and c) dehydrating the resulting composition to less than or equal to 1.5% water.

In a preferred embodiment of the method, the step of heating comprises the sequential steps of: a) heating the mixture to 170° F. for 10 minutes; b) heating the mixture to 180° F. for 15 minutes; and c) heating the mixture to 190° F. for 3 to 5 hours, until no insoluble material is visible to the naked eye.

In a preferred embodiment of the method, the mixture of step (a) comprises one mass unit of zinc oxide, about 2.5 mass units of aspartic acid, and about 64.5 mass units of high fructose corn syrup.

In a further preferred embodiment of the method, the high fructose corn syrup has the following characteristics: a) about 77% solids and 23% moisture; and b) a carbohydrate composition as follows: about 55% fructose, about 41% dextrose, with the remainder being higher saccharides.

The invention further encompasses a method of reducing the duration of symptoms of viral infection, the method comprising the step of administering a therapeutically effective amount of a composition comprising a chemical compound selecting form the group consisting of structures 1–4 or an analog thereof having antiviral activity, such that the duration of the symptoms is reduced.

In a preferred embodiment, the virus is one which causes the common cold.

In another preferred embodiment, the virus is herpes zoster (varicella zoster).

The invention further encompasses a method of reducing the titer of a virus in a virally infected individual, the method comprising the step of administering a therapeutically effective amount of a composition comprising, selected from the group consisting of structure 1–4 an analog thereof, such that the titer of the virus in the individual is reduced.

The invention further encompasses a method of increasing the number of CD4$^+$ T cells in an individual infected with human immunodeficiency virus, the method comprising the step of administering a therapeutically effective amount of a composition selected from the group consisting of structure 1–4 an analog thereof, such that the number of $CD4^+$ T cells is increased.

The invention further encompasses a method of maintaining the number of $CD4^+$ T cells in an individual infected with human immunodeficiency virus, the method comprising the step of administering a therapeutically effective amount of a composition selected from the group consisting of structure 1–4 an analog thereof, such that the number of $CD4^+$ T cells is maintained.

The invention further encompasses a method of reducing the size of a tumor in an individual, the method comprising the step of administering a therapeutically effective amount of a composition selected from the group consisting of structure 1–4 an analog thereof, such that the size of the tumor is reduced.

In preferred embodiments of the methods of reducing the duration of symptoms of viral infection, reducing the titer of a virus, increasing or maintaining $CD4^+$ T cells, or reducing the size or cellular load of a tumor, the composition is administered transmucosally.

In other preferred embodiments of the methods of reducing the duration of symptoms of viral infection, reducing the titer of a virus, increasing or maintaining $CD4^+$ T cells, or reducing the size or cellular load of a tumor, the composition is administered parenterally.

The invention further encompasses a kit for performing the methods of reducing the duration of symptoms of viral infection, reducing the titer of a virus, increasing or maintaining $CD4^+$ T cells, or reducing the size or cellular load of a tumor.

As used herein, the term "antiviral activity" refers to the ability of a composition or treatment regimen to ameliorate the symptoms of a viral infection. Intiviral activity includes, but is not limited to an activity resulting in a reduction by at least 10% in viral titer or a reduction by at least 10% in the severity or duration of the symptoms of a viral infection. The symptoms of a viral infetion include not only those directly caused by viral replication and accompanying cell death, but also secondary symptoms, such as those caused by opportunistic bacterial infections that occur subsequent to the death of infected cells.

As used herein, the term "analog" refers to a composition that varies from an original or primary composition by the presence of one or more chemical additions, deletions or substititions not present in the structure of the primary composition. An analog as used herein will have at least 50% of the antiviral or antitumor activity of the primary composition, and preferably more, up to and exceeding 100% of the activity of the primary composition. An analog may have physical or functional characteristics that differ from those of the primary composition, for example, different or enhanced solubility, membrane permeability, or biological half-life, while retaining anti-viral or anti-tumor activity. The term "analog" also refers to a different enantiomeric form of a given compound, such as the dextrorotatory or levorotatory form of a molecule or a compound made using one or another enantiomeric forms of a given constituent. As a non-limiting example, the compositions made by mixing the D, or L enantiomeric forms of aspartic acid with zinc oxide and high fructose corn syrup as described herein would be considered analogs of the composition made using the mixed enantiomeric D+L form of aspartic acid.

As used herein, the term "high fructose corn syrup" refers to a liquid carbohydrate composition comprising at least 50% fructose by weight. The carbohydrate composition is preferably derived from corn or other vegetable or plant material. The remaining proportion may contain various relative amounts of other saccharides, including, but not limited to sucrose, dextrose and higher saccharides.

As used herein, the phrase "mixture comprising zinc oxide, aspartic acid, and high fructose corn syrup" means a combination comprising zinc oxide, the D, L, or D+L forms of aspartic acid, and high fructose corn syrup meeting the definition of high fructose corn syrup presented herein.

As used herein, the term "solids" refers to the matter present after the removal of water or solvent, such as by lyophilization or evaporation.

As used herein, the term "carbohydrate composition" refers to a mixture consisting essentially of of higher and lower saccharides. Higher saccharides include those having more than two linked carbohydrate monomers or subunits, for example, trisaccharides (three monomer subunits), tetrasaccharides (four monomer subunits) or oligosaccharides with more than four carbohydrate subunits. Lower saccharides include those with one or two carbohydrate monomers. A carbohydrate composition may initially be in the form of a solid or powdered solid, or it may initially be in the form of a liquid solution.

As used herein, the term "visible insoluble material" refers to particles of material in a solution that are visible to the naked eye, assuming natural or corrected 20/20 vision. A visible insoluble material may include particulate matter that settles near the bottom of a container holding a solution, or it may include fine particulate matter that remains in suspension but reduces the transparency of the solution. A solution or mixture with no visible insoluble material may be colored, but will be transparent, with no visually observable cloudiness.

As used herein, the term "dehydrating" refers to a process whereby water is removed from a solution or composition. According to the invention, dehydrating may be accomplished by processes including, but not limited to, freeze-drying (lyophilization), dessication under vacuum with or without heating, or dessication at atmospheric pressure with heating. A dehydrated composition of the invention will have about 5% or less, preferably about 2.5%, 1.5%, 1%, 0.5%, 0.2%, 0.1% or less of water by weight.

As used herein, the term "reducing the duration of symptoms" means that the length of time symptoms of a viral infection are present is lessened by at least 10% in a treated individual relative to an individual receiving no treatment. The time or duration of symptoms of a viral infection is the time from which symptoms first become apparent to the infected individual until such symptoms are not apparent to the same individual (i.e., symptoms are fully resolved).

As used herein, the term "administering" refers to a process whereby a composition of the invention is introduced to the body of an individual in need of treatment. Administration may, for example, be by way of absorption through oral or other (e.g., rectal or vaginal) mucosa (referred to herein as "transmucosal" delivery or administration. Alternatively, administration may be by intramuscular, intravenous or intraperitoneal delivery means, which are collectively referred to herein as "parenteral" administration or delivery. Topical administration, for example for the treatment of shingles, or other viral infection affecting the skin, is not excluded from the meaning of "administering" presented herein.

As used herein, the term "therapeutically effective amount" refers to the amount of a composition of the invention necessary to reduce the symptoms of a viral infection by at least 10%, to slow or halt the growth of a tumor, or to reduce the size of a tumor by at least 10%. A therapeutically effective amount may be delivered over a period of days, weeks or longer in order to have the desired therapeutic effect.

As used herein, the term "common cold" refers to the disease symptoms resulting from infection with members of the rhinovirus family. Symptoms can include any or all of sore throat, cough, nasal congestion, runny nose, sneezing, swollen glands, muscular achiness and fever.

As used herein, the term "reducing" or "reduced" when used to refer to the titer of a virus in an infected individual means that the titer of virus is lessened by at least 10%, and preferably by 20%, 30%, 50%, 70%, 90% or more, up to and including 100% (i.e., no detectable virus present).

As used herein, the term "maintaining the number of $CD4^+$ T" cells refers to the situation in which treatment according to the invention results in no fluctuation (increase or decrease by up to 5%) in the number of CD4+ T cells in a given volume of peripheral blood over a period of at least one week. Preferably, CD4+ T cell counts are maintained for months or even years or decades following commencement of treatment.

As used herein, the term "increasing the number of $CD4^+$ T" cells refers to the situation in which treatment according to the invention results in an increase in the number of $CD4^+$ T cells relative to the number of $CD4^+$ T cells present prior to the commencement of treatment, with the increase being at least 5%, and preferably as much as 10%, 20%, 30%, 50%, 75%, or even 100% or more, up to and surpassing 500 $CD4^+$ T cells per microliter of blood.

As used herein, the term "Human Immunodeficiency Virus" or "HIV" is meant to refer to all strains of human immunodeficiency viruses. Active human immunodeficiency virus infection results in a decline in the number of $CD4^+$ T cells, which in turn results in the incapacity of the infected individual to mount an effective immune response to viral, bacterial, fungal or parasitic infections.

As used herein, the term "reducing the size of a tumor in an individual" means that the size of a solid tumor or the load of tumor cells from a non-solid malignancy (e.g., a leukemia) is decreased by at least 10% or more, preferably as much as 20%, 30%, 50%, 70%, 90%, or even up to and including 100% decreased (i.e., no tumor or tumor cells) relative to the tumor size or tumor cell number before treatment according to the invention.

Further features and advantages of the invention will become more fully apparent in the following description of the embodiments and drawings thereof, and from the claims.

DESCRIPTION

The invention provides compositions and methods useful for ameliorating the symptoms of individuals suffering from a viral infection, for example, infection by viruses including rhinoviruses (i.e., common cold), varicella zoster, and HIV. The symptoms of other viral infections treatable with the methods and compositions of the invention include, but are not limited to those caused by infection with Adenoviruses, Poxviruses (including vaccinia viruses, and molluscum contagiosum virus) Bunyaviruses (including Rift Valley fever virus, Sandfly fever virus, Dengue virus, and Punta Toro virus), Flaviviruses (including yellow fever virus and Japanese encephalitis virus), Herpesviruses (including cytomegalovirus (CMV), human herpesvirus-6, herpesviruses 1 and 2, and Epstein-Barr virus (EBV)), Paramyxoviruses (including respiratory syncytial virus (RSV), measles virus, parainfluenza viruses, and mumps), Orthomyxoviruses (including influenza A, B and C), Hepadnaviruses (including hepatitis A, B, C, delta and E viruses), Picornaviruses (including polioviruses, coxsackieviruses, and ECHO viruses), Rhabdoviruses (including rabies virus), Togaviruses (including Venezuelan equine encephalitis virus), Filoviruses (including Ebola virus and Marburg virus), Papovaviruses (including human papilloma viruses), Rubiviruses (including rubella virus), Orbiviruses (including Colorado tick virus, Junin and Machupo viruses), Hantaan Viruses (including Hantaan hemorrhagic fever virus and Congo/Crimean hemorrhagic fever virus), and Retroviruses and Lentiviruses (including HTLV 1 and 2, and HIV 1 and 2).

The compositions of the invention may be used either alone, or in combination with other antiviral compounds. It is anticipated that the use of the compositions of the invention in combination with other antiviral compounds will be more effective than the use of either compound alone. The broad antiviral nature of the compositions of the invention makes them well-suited for combination with antiviral drugs having narrower spectra of activity, such as the anti-retroviral drugs AZT, ddI, ddC, the retroviarl protease inhibitors, or the anti-herpesvirus drugs acyclovir or gancyclovir. This type of combination therapy may be useful, for example, in limiting the development of resistance to the narrow spectrum drugs, as well as simply enhancing the efficacy of the narrow spectrum drugs.

Figure 1:
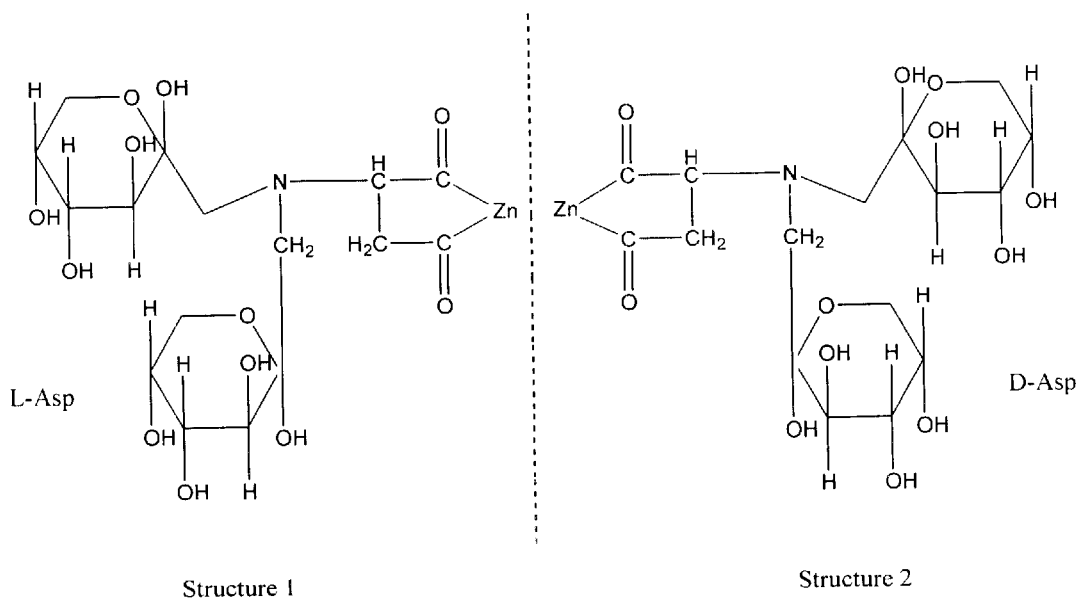
FIG. 1 shows the chemical structures of the active compounds of composition A (structures 1–4).
Figure 1:
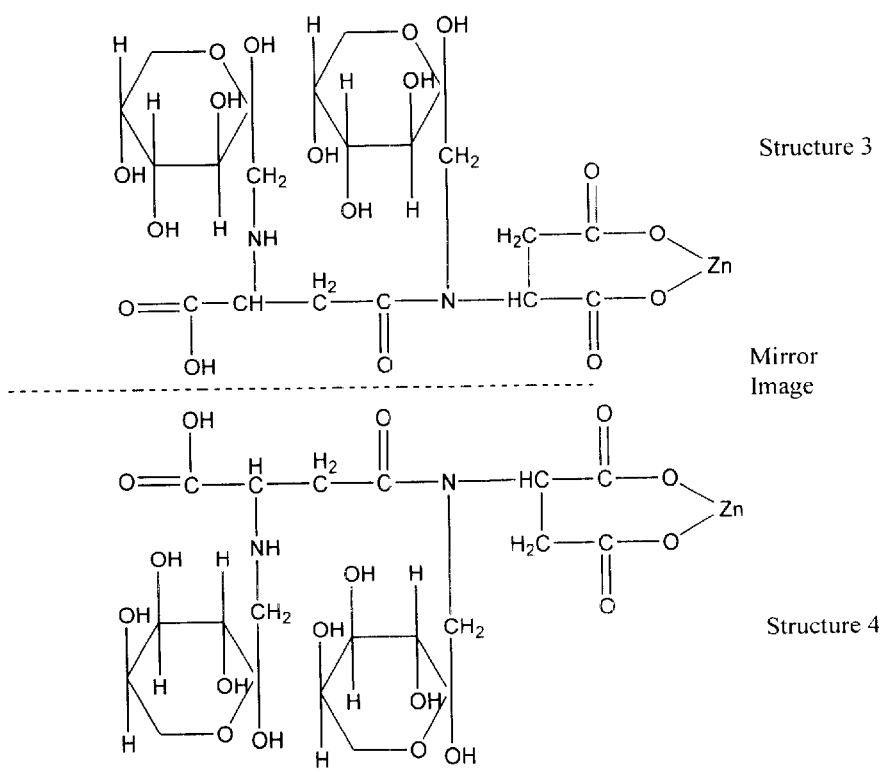

The chemical structure of one embodiment of the invention is shown in FIG. 1. This composition is produced from the starting components zinc oxide (ZnO), D+L aspartic acid, and high fructose corn syrup as described below. Two additional compositions, comprising Structures 2 and 3, respectively, are produced using the essentially pure D or L forms of aspartic acid in place of the mixed enantiomer D+L form and contain only the respective D or L enantiomeric forms of the resulting zinc-aspatate-sugar composition of the invention.

I. How to Make Compositions Useful for the Reduction of Symptoms of Viral Infection According to the Invention The primary components used to produce the anti-viral compositions of the invention are zinc oxide, aspartic acid (D+L form or essentially enantiomerically pure D or L forms), and high fructose corn syrup. Zinc oxide and mixed enantiomer aspartic acid are widely available, as are essentially enantiomerically pure preparations of D or L aspartic acid.

High fructose corn syrup used in the production of the anti-viral compositions is also widely available, although the exact compositions of the various products vary depending upon the specific source. For use in the production of compositions according to the invention, high fructose corn syrup having approximately the following characteristics is most preferred:

1) 77% solids and 23% moisture
2) Carbohydrate composition:
   55% Fructose
   41% Dextrose
   4% higher saccharides:
      For example,
         1.87% disaccharide ($C_{24}H_{44}O22$)
         1.49% trisaccharide ($C_{19}H_{35.2}O_{17.6}$)
         0.37% quadsaccharide ($C_{4.8}H_{8.8}O_{8.8}$).

One commercially available high fructose corn syrup that is suited for use in producing the compositions of the invention is ISOSWEET® 5500 (Staley; Decatur, Ill.). However, the invention is not intended to be limited to the use of this particular corn syrup formulation. In fact, not only may the proportions of each of the various components in the corn syrup preparation vary by about 20% (higher or lower than the proportions listed), essentially pure fructose (i.e., at least about 95% or more fructose) may be used as well. Similarly, other higher order sugars, dissolved in water, may be used, as long as the ZnO and aspartic acid components remain completely soluble after the formulation is prepared in lozenge form. It is noted, however, that when pure dextrose was used to prepare a test composition, the resulting composition was not active in the amelioration or reduction of the symptoms of viral infection. Therefore, it is preferred that fructose or higher order sugars be used in the preparation of the compositions of the invention.

Figure 2:
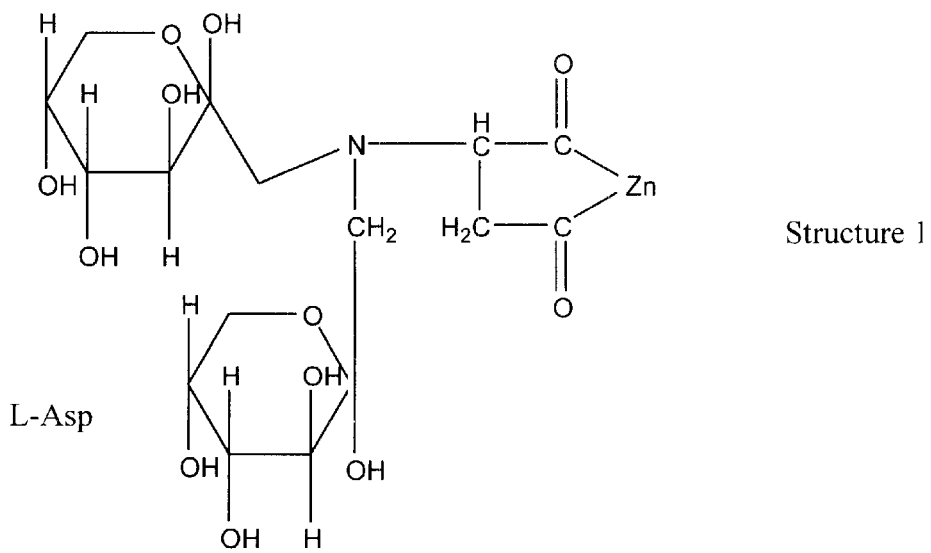
FIG. 2 shows the chemical structures of the active compounds of compositions B (structures 1 and 3).
Figure 2:
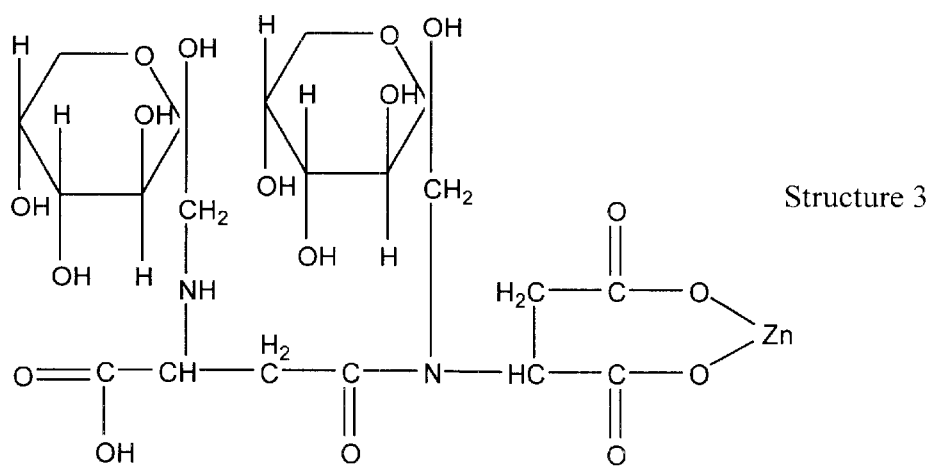
Figure 3:
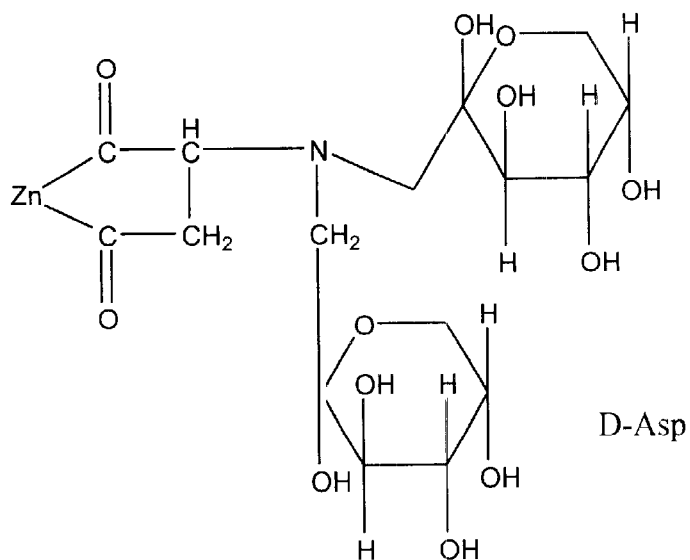
FIG. 3 shows the chemical structures of the active compounds of compositions C (structures 2 and 4).
Figure 3:
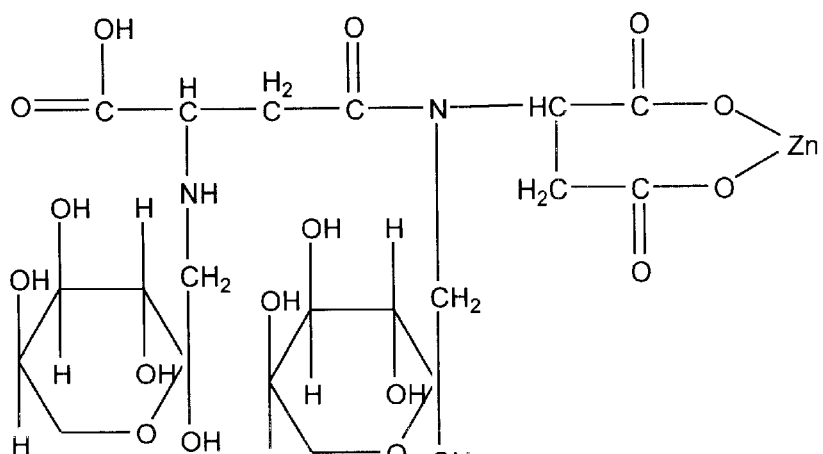

The following describes the steps one may take to make anti-viral Composition A according to the invention. This process results in the preparation of mixed enantiomer (D+L) forms of the composition, i.e., the composition including structures 1–4 presented in FIG. 1. The use of essentially enantiomerically pure D or L forms (i.e., about 95% or more of one enantiomer) in the same proportions of ingredients and the same process steps will generate the Compositions B (L form of aspartic acid used, resulting in a composition including structures 1 and 3; see FIG. 2) and C (D form of aspartic acid used, resulting in a composition including structure 2 and 4; see FIG. 3).

Steps for the preparation of antiviral Composition A:

1) Combine one part (by weight) zinc oxide, ZnO, with 2.5 parts D+L aspartic acid, 64.5 parts high fructose corn syrup as described, and, optionally, 5.5 parts distilled water; for example, combine 13.7 g of ZnO, 33.8 g D+L aspartic acid, 883.4 g Staley Isosweet® 5500, and, optionally, 75 g distilled water;
2) Heat the combination with stirring for 10 minutes at 170° F. (mixture will be light yellow in color);
3) Heat to 185° F. for 15 minutes;
4) Heat to 190° F. for 3 to 5 hours (reaction is complete when no insoluble material is visible to the eye and the color of the composition changes to dark brown);
5) The composition is then dehydrated to less than or equal to 1.5% $H_2O$, preferably about 1% or less, 0.75% or less, 0.5% or less, 0.3% or less, and most preferably about 0.2% water by weight by heating at about 145° F. in a dehydrator. For the dehydration step, it is preferred, although not absolutely necessary, that the composition be placed on silicone release paper to facilitate the subsequent step of forming lozenges.

The proportions of each ingredient in the composition may be varied (increased or decreased) by about 20% and still result in a composition with some anti-viral or anti-tumor activity. That is, the formulation presented above represents the most effective combination of ingredients known, but varying the amounts of aspartic acid and/or zinc oxide within about 20% of the stated proportions will produce an active composition, provided the solubility of the ingredients is maintained. Specifically, it is noted that increasing the proportion of zinc oxide results, at least with the high fructose corn syrup and aspartic acid preparations tried, in precipitation of solids as the composition is dehydrated, or in the failure to obtain complete solubilization in the first place. That is, while proportions of the ingredients may be varied over the stated ranges, it is preferred that there be no precipitation of solids during the preparation of the compostions.

Following dehydration, the composition is rolled or pressed into lozenges (generally, lozenges comprise about 1 gram of the composition, although larger or smaller lozenges may be made for particular applications). Alternatively, the composition may be dissolved in a suitable carrier (e.g., buffered saline or other pharmaceutically acceptable solution) for injection or mixed with other suitable pharmaceutical carriers (e.g., surfactants, lubricants, etc.; see "Administration and Dosages", below) for other routes of administration.

An example of how to make a preparation containing Composition A for parenteral administration is as follows (the same steps are followed to prepare Compositions B and C for parenteral administration). 100 grams of the dehydrated (about 0.2% water) Composition A prepared as described above are dissolved in 1.5 liters of ultrapure water with USP NaCl to make an isotonic solution (i.e., about 2.8 grams). The final composition is about 6.24% of the antiviral composition by weight. Two parts of this preparation are mixed with one part of xylocaine (e.g., 2 ml antiviral composition plus 1 ml xylocaine) immediately prior to administration.

Analogs

Analogs of the active constituents of antiviral Compositions A (Structures 1–4, shown in FIG. 1) include those variants that possess antiviral activity, that result from the use of essentially enantiomerically pure D or L aspartic acid in the preparation of the composition.

Other analogs of the compounds of Structures 1–4 include, but are not limited to those with substituents on the carbohydrate(s), such as alkyl or aryl groups, which may, for example, enhance membrane permeability. Other analogs include those with charged or polar substituents (e.g., phosphate or phosphonyl or sulfate or sulfonyl-containing substituents) which may enhance water solubility. It is understood that one skilled in the art of synthetic orgainc chemistry may synthesize such analogs as desired from readily available precursors.

Essentially, any substituent may be added or changed, including wholesale replacement of the fructose with other saccharides or saccharide polymers, as long as the change does not displace the zinc constituent of the compound and the compound continues to have antiviral activity as defined herein.

Methods of Assessing Viral Titer and the Antiviral Activity of Analogs of the Compounds of Structures 1–4

A plaque-formation assay to monitor viral titer involves the addition of a known amount of serum from an infected individual to a monolayer culture of cells susceptible to infection by the virus being titered. If a particular virus being treated does not appear in the serum of infected individuals during the normal course of infection, the viral titer may be measured by swabbing the infected tissue with an absorbent material and measuring the amount of virus removed on the swab. As used in this context, an individual may be a human or an animal, including an experimental animal, such as a mouse, rat, rabbit, goat, etc. Following incubation for a period of time that will also vary with the cell type and virus, monolayers are either stained with a vital stain (i.e., a stain, such as trypan blue that is differentially taken up or excluded by viable, versus non-viable cells), or fixed and stained (e.g., with Giemsa stain). In either case, staining serves to visualize plaques caused by viral infection of cells of the monolayer. The number of plaques arising with a given amount (or dilution) of serum or solution prepared from a swab represents the titer of that virus in that sample. Samples taken before, during, and after treatment with compositions of the invention may be compared to titers taken from similar infected, untreated individuals at similar times after infection. The titer is reduced if, at a given point following treatment, it is at least 10% less in a treated individual than in an untreated individual, and preferably if the titer is lessened by 20%, 30%, 50%, 70%, 90% or more, up to and including 100% (i.e., no detectable virus present) lower than the titer in the untreated individual.

The following describes a more specific example of a plaque-formation viral titer assay, designed to measure the titer of respiratory syncytial virus (RSV) particles in infected African green monkeys. Monkeys are infected by administration of viral stocks by either intratracheal catheter or by intranasal instillation. Throat swabs are taken daily and placed in 1.0 ml of tissue culture medium (for example, Dulbecco's Minimal Essential Medium with 10% fetal bovine serum and antibiotics). Titrations are performed on the 1.0 ml sample of medium after expression of fluid from the swab, using serial ten-fold dilutions of the sample. Each dilution is inoculated into duplicate wells of a 24 well plate containing monolayer cultures of BSC-40 cells. The titers are obtained by microscopic examination of the cultures for viral induced cytopathology (i.e., plaques). Samples to be titered may also be obtained through bronchoalveolar lavage; titer procedures are essentially the same as for throat swabs.

One approach to measuring viral titer by cell viability uses the vital indicator 3-(4,5-dimethylthiazol-2-yl)-2,5-diphenyltetrazolium bromide (MTT), which is reduced by viable cells. Reduction of MTT results in a calorimetric change that may be monitored either visually or by spectrophotometry. Since only viable cells reduce MTT, comparisons of the optical density of medium from infected versus non-infected cells reflect the killing of cells by a virus. The MTT assay has been used to measure viral titers using both non-adherent (Pauwels et al., 1988, J. Virol. Meth. 20: 309) and adherent (Takeuchi et al., 1991, J. Virol. Meth. 33: 61) cells.

The MTT assay is also well suited for the assessment of the efficacy of antiviral compounds, as shown by both Pauwels et al. (1988, supra) and Takeuchi et al. (1991, supra), both of which references are hereby incorporated by reference. This methodology may therefore be used to assess the antiviral activity of an analog of the compound of FIG. 1A. Essentially, two separate identical cultures of virally infected cells may be cultured in the presence of MTT, with one of the two cultures further containing an antiviral composition. Both cultures are then spectrophotometrically monitored for reduction of MTT. A higher level of MTT reduction in the sample with the antiviral compound indicates higher cell viability and therefore an effect of the antiviral compound against the virus. A composition (e.g., an analog of the compound having a structure shown in FIG. 1) is effective as an antiviral agent in this assay if the MTT reduction is increased by at least 10% in an infected culture containing the composition, relative to the MTT reduction detected in an infected culture without the compostion. The concentration of an antiviral composition necessary to inhibit the cytopathic effect (as measured by MTT reduction) of a virus by 50% is termed the $IC_{50}$ for that composition. An analog identified as having antiviral activity in this type of assay may then be tested for toxicity according to methods known in the art before ultimately being tested in human trials for antiviral efficacy.

For any analysis of analog antiviral activity, it is assumed that test results are either compared with results obtained using similar amounts of the compound of Structure 1 or that the compound of Structure 1 (or the compound of Structure 1 in the form of composition A) is tested in side-by-side assays with the analog.

Another method for monitoring the efficacy of an anitviral composition is to monitor the number of viral target cells present in vivo before and after treatment with the composition. This type of assay is well suited for measurement of viruses such as HIV, which infects and kills $CD4^+$ T lymphocytes normally present in the circulation. Thus, an increase in $CD4^+$ T cells in an individual infected with a virus that kills $CD4^+$ T cells, following treatment with an antiviral composition or analog compound, indicates that the composition or analog compound is effective against that virus.

II. How to Use the Antiviral Compositions of the Invention

A. Dosage and Administration

The compositions of the invention may be administered in a number of different ways. Preparations comprising compositions A–C may be administered through oral (i.e., transmucosal), rectal, transdermal (i.e., topical), vaginal and parenteral (including sub-cutaneous, intramuscular and intravenous) routes. The choice of the particular route will depend upon the nature and severity of the viral disease being treated, and may be adjusted or altered by the administering physician to suit a particular patient's needs. Generally, more severe or advanced infection is treated with parenteral administration either with or without additional transmucosal administrations.

A preferred route of administration is passage across the oral mucosa. In this format, one or more lozenges (e.g., comprising Composition A) as described above are placed along the gumline and allowed to dissolve slowly, generally over 30 minutes to one hour. This route of administration is simple, effective, and requires no sterile apparatus such as hypodermic needles, syringes or IV equipment. Dosages may be increased or decreased by simply increasing or decreasing the number of such lozenges administered, as needed. It is preferred, although not absolutely necessary, that oral transmucosal administration should be performed within approximately 30 minutes to one hour following a meal, to reduce the risk of gastrointestinal upset.

For oral transmucosal drug delivery, dosage and frequency of administration will vary with the severity and nature of the viral infection. Generally, however, the initial dose may be one lozenge, administered as above, three times daily, until the desired clinical effects (e.g., reduced disease symptoms, reduced viral titer, increased CD4 levels, reduced tumor size, etc.) are achieved.

Another preferred route of administration is parenterally via injection. A composition of the invention may be dissolved in a suitable pharmaceutical carrier solution (for example, sterile buffered saline or sterile, pyrogen-free water, as described above. It is specifically noted that dissolving the compositions of the invention in dimethyl sulfoxide (DMSO) results in inactivation of the compositions. Therefore, it is preferred that DMSO not be used for preparation of the compositions for parenteral administration. While not wishing to be bound by any single theory, it is possible that the metal chelating activity of DMSO is responsible for the inactivation of the compositions. Therefore, it is also preferred that the use of other chelators, such as EDTA, be avoided in the preparation of solubilized compositions of the invention.

It is further preferred, although not absolutely necessary that for intramuscular injection in particular, and parenteral administration in general, an anesthetic, such as xylocaine or lidocaine, be added to the preparation in order to avoid local discomfort at the site of the injection.

For parenteral administration, the dose and frequency of administration will vary with the particular viral disease being treated. Dosages may be increased or decreased by the administering physician as deemed medically necessary or advantageous to achieve the desired therapeutic effect. As an example, the preparation described above for parenteral administration (2 parts of 6.24% anti-viral composition to 1 part anesthetic) may be administered once every two days for six days (i.e., 3 doses). This dosage regimen was effective in increasing the CD4+ T cell counts of a number of individuals with active HIV (see examples, below).

The parenteral administration may be combined with transmucosal administration if desired. For example, one dosing regimen found to be effective consisted of injection twice per week for 5 weeks with the parenteral antiviral composition/anesthetic formulation described above, in addition to oral transmucosal delivery of about 1 gram of the lozenge form of the same antiviral composition every day, three times a day after meals over the same period.

B. Toxicity

There is no indication of local or systemic toxicity of Compositions A–C of the invention in humans or in animals when administered in the dose and frequency ranges described above. In addition to the human trial data described below, Swiss-Webster mice injected intraperitoneally twice daily for 8 days with 0.05 ml of the Composition A formulation described above or a 1:10 dilution of it showed no signs of disease or death.

C. Monitoring the Antiviral Efficacy of the Compositions of the Invention

The therapeutic efficacy of the compositions of the invention may be monitored in several ways. First, the symptoms of infected individuals may be monitored. It is acknowledged that the symptoms of viral infections treatable with the compositions of the invention will vary with the specific virus, and to some extent, with the individual infected. However, the average duration of symptoms for a given viral infection in humans or in animals is known in the art. A reduction in the duration of symptoms as compared with duration in cases not treated with a composition of the invention is evidence of an effect of the composition against the viral symptoms. According to the invention, the duration of symptoms is reduced if symptoms are fully resolved (i.e., absent) at least 10% sooner in patients treated with a composition of the invention than in untreated patients infected with the same virus.

For treatment of the common cold (i.e., rhinovirus infection) a composition according to the invention is administered to a patient in approximately one gram doses by the oral transmucosal route, generally three times a day, following meals, for a time sufficient to have a therapeutic effect. Symptoms of rhinovirus infection, including coughing, fever, nasal congestion or runny nose may be readily quantitated and are useful for monitoring the effectiveness of treatment. As used herein, symptoms of the common cold are considered reduced or decreased if any one of coughing, sneezing, fever, or nasal congestion/runny nose are reduced or decreased by at least about 10% or more following administration of a composition of the invention according to the dosing regimen described. Bouts of coughing, counted as coughs per hour are decreased according to the invention if they are reduced in number by at least 10% following treatment, preferably by at least 20%, 30%, 50%, 70%, 90% or more, up to and including 100% (i.e., no coughs per hour), relative to coughing prior to administration of a composition of the invention. The defining parameters for reduced sneezing are the same as those for reduced coughing.

Fever is reduced or decreased according to the invention if it is reduced by 0.5° F. or more, 1° F., 1.5° F., 2° F., 3° F., 4° F. or even 5° F. or more, down to and including normal body temperature of 98.6° F. (37° C.), relative to temperature before treatment according to the invention.

Nasal congestion or runny nose is decreased if the number of times an infected individual blows their nose per hour decreases by at least 10% or more, preferably by at least 20%, 30%, 50%, 70%, 90% or more, up to and including 100% (i.e., no nasal congestion/runny nose).

Additional symptoms of the common cold include sore throat and swollen glands, both of which are difficult to quantitate, however it is clear to an individual whether their throat is sore or not, and swollen glands may be readily detected by palpation. These symptoms are also of use in monitoring the efficacy of treatment methods according to the invention.

For the amelioration or reduction of the symptoms of shingles (varicella zoster virus infection), a composition according to the invention is administered to a patient in approximately one gram doses by the oral transmucosal route, generally three times a day, following meals, for a time sufficient to have a therapeutic effect. According to the invention, the symptoms of shingles are considered reduced if the lesions are at least 10% smaller, preferably 20%, 30%, 50%, 70%, 90% or up to and including 100% smaller (i.e., no lesion) following treatment, relative to the size of lesions before treatment. Alternatively, shingles are considered reduced or ameliorated if the number of lesions is at least 10% fewer, preferably 20%, 30%, 50%, 70%, 90% or even up to and including 100% fewer (i.e., no lesions) following treatment, relative to the number of lesions present before treatment.

For the treatment of HIV, especially for maintaining or increasing the CD4+ T cell count in an individual infected with HIV, an antiviral preparation according to the invention is administered either parenterally or transmucosally or via both routes as described herein, and CD4+ T cells are quantitated according to standard methods known in the art. The Centers for Disease Control has established the following levels of CD4+ T cells as indicative of the various stages of Acquired Immune Deficiency Syndrome (AIDS) in those infected with HIV. A CD4+ T cell count of 500 per microliter or more correlates with the asymptomatic stage of the disease. A CD4+ T cell count of 499–200 per microliter is associated with early symptoms of the disease, and a count of less than 200 per microliter is associated with severe immunosuppression. A count of 499 or fewer is referred to herein as "active disease". Preferably, a treatment that maintains or increases CD4+ T cell counts will keep an infected individual's CD4+ T cell count above 200 per microliter or more, and more preferably above 500 per microliter. The compositions of the invention are useful for both maintaining and increasing CD4+ T cell counts; the compositions may be administered to healthy infected individuals to maintain counts, or they may be administered to infected individuals with active disease in order to increase counts.

According to the invention, an individual's CD4+ T cell count is considered to be maintained if it does not fluctuate (increase or decrease by up to 5%) over a period of 1 week or more in an HIV+ individual. According to the invention, an individual's CD4+ T cell count is considered to be increased if the number of CD4+ T cells increases by 5% or more, preferably by 10%, 20%, 30%, 50%, 70%, 90%, 100% or more, up to and preferably exceeding 500 CD4+ T cells per microliter following administration of an antiviral composition of the invention.

In addition to monitoring CD4+ T cell counts, the efficacy of the treatment methods of the invention in HIV infected individuals may be measured by monitoring the titer of the virus itself. Methods of measuring HIV viral titer are well known in the art. The monitoring of clinical efficacy of the treatment of other viruses with the methods of the invention may also be performed by measurement of titers of those viruses in infected individuals. Methods of measuring viral titer are known in the art. Some methods vary with the specific virus, since individual viruses have differing host cell type specificities. Generally, however, viral titer may be measured by plaque-formation assays, or by cell viability assays. Viral titer, and thereby viral disease, is considered to be reduced according to the invention if it decreases by at least 10%, preferably by at least 20%, 30%, 50%, 70%, 90% or more, up to and including 100%, or the lack of virus in the individual following treatment with a composition of the invention.

Compositions according to the invention can also be useful in the treatment of tumors. One broad class of tumors that the compositions of the invention are expected to be particularly active against is the virus-related tumors. Viruses associated with tumor development include, but are not limited to the following: HIV (associated with B-cell lymphomas, cervical lymphomas, Hodgkin's disease, T cell lymphomas and Kaposi's sarcoma); Epstein-Barr virus (EBV, associated with Burkitt's lymphoma and other B cell lymphomas, Hodgkin's disease and nasopharyngeal carcinoma); Hepatitis B and C viruses (associated with hepatocellular carcinoma); Human Papillomavirus (associated with cervical carcinoma); and Human T Cell Leukemia virus-1 (HTLV-1, associated with T cell leukemias). It is noted herein that while opportunistic infection is a leading ultimate cause of death in AIDS patients, HIV-related tumors are responsible for a significant number of HIV-related deaths. Evidence is presented in Example 5 that HIV-related tumors may be reduced in size using the compositions and methods of the invention. This is in no way meant to exclude non-viral-related tumors from those that may be treated with compositions or methods of the invention.

Administration of a composition according to the invention by parenteral or transmucosal routes or both as described herein can halt the growth of a tumor or reduce its size or the number of tumor cells (tumor cell load) in an individual. Tumor size may be measured in a number of ways, including for example, external palpation, X-ray, ultrasound, magnetic resonance imaging or radiographic imaging using tumor-marker specific imaging agents. For non-solid tumors, such as lymphomas or leukemias, the number of abnormal cells can be directly measured, for example in samples of the blood or bone marrow. According to the invention, tumor growth or the proliferation of cancer cells is considered to be halted or stopped if the size of the tumor or the number of abnormal cells present in a sample does not increase over a period of one week or more, preferably 2 weeks or more, 1 month, 6 months, one year or preferably 2 years or more following administration of a composition according to the invention to an individual in need of such treatment. Alternatively, the size of a tumor or the number of tumor cells is considered to be decreased according to the invention if it is at least 10% less, preferably 20%, 30%, 50%, 70%, 90% or even up to and including 100% less (i.e., no tumor or tumor cells) than the size of the tumor or the number of cells present prior to commencement of treatment.

EXAMPLE 1

Reduction of the Symptoms of the Common Cold

The composition made according to the methods described herein using D+L aspartic acid, ZnO and high fructose corn syrup (referred to herein as Composition A) was tested for efficacy in reducing or ameliorating the symptoms of the common cold by administering it to 14 different volunteer subjects in 23 different instances in which they reoprted symptoms of the common cold. Their symptoms included sore throat, congestion or runny nose, sneezing, cough, swollen glands, and laryngitis. In each instance, the volunteers were given three doses of Composition A over a period of 3 hours to one day. In each instance, the subjects reported amelioration of symptoms, all stating that the cold symptoms were gone completely in periods ranging from 2 hours to overnight. The individual results are presented below in Table 1. It is clear from these results that Composition A is effective in ameliorating the symptoms of the common cold.

TABLE 1

Results of Trials of Composition A Against the Common Cold

| SUBJECT | SORE THROAT | COUGH | CONGESTION RUNNY NOSE | SNEEZING | SWOLLEN GLANDS | COMPOSITION "A" TREATMENT | OUTCOME |
|---|---|---|---|---|---|---|---|
| 1. | X | | | | | 3x/d, 1 d | NO SYMPTOMS W/IN 2 HR TO O/N |
| 2. | | | X | X | | 3x/d, 1 d | " |
| 3. | | X | X | X | | 3x/d, 1 d | " |
| 4. | X | | X | | X | 3x/d, 2 d | " |
| 5. | X | | | | | 1x/d, 1 d | " |
| 6. | X | | | | | 2x/d, 1 d | " |
| 7. | X | | | | | 1x/d, 1 d | " |
| 8. | X | X | | | | 2x/d, 1 d | " |
| 9. | X | X | | | | 2x/d, 1 d | " |
| 10. | | | X | | | 3x/d, 1 d | " |

TABLE 1-continued

Results of Trials of Composition A Against the Common Cold

| SUBJECT | SORE THROAT | COUGH | CONGESTION RUNNY NOSE | SNEEZING | SWOLLEN GLANDS | COMPOSITION "A" TREATMENT | OUTCOME |
|---|---|---|---|---|---|---|---|
| 11. | X | | | | | 2x/d, 1 d | " |
| 12. | X | | | | | 1x/d, 2 d | " |
| 13. | X | | | | | 3x/d, 1 d | " |
| 14. | X | | | | | 3x/d, 1 d | " |
| 15. | X | X | | X | | 3x/d, 1 d | " |
| 16. | X | X | X | X | | 2x/4, 1 d | " |
| 17. | | X | X | | | 3x/d, 1 d | " |
| 18. | X | X | | | | 1x/d, 1 d | " |
| 19. | X | X | X | | | 2x/d, 1 d | " |
| 20. | X | X | X | | | 2x/d, 1 d | " |
| 21. | | | X | | | 3x/d, 1 d | " |
| 22. | X | | | | X | 2x/d, 1 d | " |

EXAMPLE 2

Ameliorating the Symptoms of Varicella Zoster Infection (Shingles)

Varicella zoster is the Herpes virus responsible for both chickenpox and shingles. Following infection with the virus, most often in childhood, individuals develop chickenpox. In some cases, after the initial infection, the virus may remain dormant in infected nerve ganglia for years, and often for decades, before re-activating to cause the painful lesions commonly known as shingles. In order to test the effectiveness of the antiviral compositions of the invention on the symptoms of this viral illness, Composition A was administered to two different patients, each of whom had two separate diagnosed attacks of shingles on different occasions, for a total of four separate cases of shingles. In each case, Composition A was administered in lozenge form for transmucosal delivery, about 1 gram per lozenge, 3 times per day after meals by slowly dissolving the lozenge along the gumline. Within 3 to 4 days of the initial treatment, in each case the patients reported amelioration of the symptoms. Treatment was continued for 7 to 10 days, after which symptoms had completely ceased and the lesions had largely disappeared. In one instance, the diagnosing physician, upon a follow-up examination 10 days after the initial visit expressed amazement at the degree of recovery.

EXAMPLE 3

Maintaining or Increasing CD4+ T Cells in Individuals Infected with HIV

In order to test the efficacy of the antiviral compositions of the invention on HIV infection, HIV-infected volunteers in the AIDS-stricken country of Haiti were given Composition A, via both parenteral and transmucosal delivery routes as described herein below, and the general health and CD4+ T cell counts of the patients were monitored.

A composition for intravenous administration was prepared as follows. 100 grams of the dehydrated (about 0.2% water) Composition A, prepared as described herein above using the D+L forms of aspartic acid, were dissolved in 1.5 liters of ultrapure water with USP NaCl to make an isotonic solution (i.e., about 2.8 grams of NaCl). The final composition is about 6.24% of the antiviral composition by weight. Two parts of this preparation are mixed with one part of xylocaine (e.g., 2 ml antiviral composition plus 1 ml xylocaine) immediately prior to intravenous administration. Dosage is generally 3 ccs per injection.

1. A 50 year old male patient, designated JF, was HIV positive and had a CD4 count of 240 (active disease) at the commencement of treatment. The patient was given 3 ccs of the Composition A/xylocaine mixture detailed above intramuscularly three times per week for three months. At the end of one month, the patient's CD4+ T cell count was $240/\mu l$, which increased to $546/\mu l$ by the end of two months, and $993/\mu l$ by the end of three months. The patient was still alive 5 years after initial treatment.

2. A 31 year old female designated KA, was HIV positive and had a CD4+ T cell count of 640 at the commencement of treatment. She received 3 ccs of Composition A by intramuscular injection three times per week for three months. After the first 44 days of treatment, her CD4 count was $993/\mu l$.

3. A 31 year old female designated AMK, was HIV positive and had a CD4+ T cell count of 640 at the commencement of treatment. The initial treatment was Composition A in lozenge form three times per day transmucosally for seven months. After five months of this initial treatment, her CD4+ T cell count was maintained at $640/\mu l$, and at the end of the first seven months her CD4 count was $854/\mu l$. At the end of the first seven months of treatment, the patient began receiving, in addition to the continued transmucosal doses of Composition A, 3 ccs of Composition A by intramuscular injection twice per week for the next three months. At the end of the first month on the combined IM and transmucosal delivery, her CD4 count was $860/\mu l$, and at the end of the third month (ten months total treatment time), her CD4 count was $820/\mu l$.

After 11 months of total treatment time, due to political unrest, it was impossible to maintain the supply of Composition A to the clinic in Haiti, and a period of five and one half months elapsed before treatment could be re-started. During the time without treatment, the patient's CD4+ T cell count declined to $570/\mu l$. Upon the re-administration of Composition A by the transmucosal delivery route three times per day, the patient's CD4+ T cell count increased to $860/\mu l$ over two months. In an additional two months, the patient's CD4 count was 820. The patient was in apparently good health, with no opportunistic infections reported two months later, at which time treatment was again discontinued. One year after this second discontinuation of treatment, the patient's CD4 count was 640, and the patient continued in good health.

It is apparent from the data obtained in this study that Composition A can increase the CD4+ T cell count in an HIV-infected individual and maintain an increased level over a period of at least 22 months. It significant, from the results of withdrawal and re-administration of the drug (due to circumstances beyond the control of the clinicians involved), that the level of CD4+ T cell counts repeatedly responds in a manner that correlates with the use of the drug.

4. An HIV positive patient, the 7 year old son of patient AMK, was treated with transmucosal Composition A for over a year. The patient's initial CD4 count was not known due to lack of availability of assay reagents, but he had a recent history of varicella zoster infection, an opportunistic infection common among HIV patients with active disease. After approximately one year on Composition A, treatment was discontinued. Eight months later, his CD4 count was 622, and he was in apparent good health, with no further opportunistic infections.

5. An HIV positive 23 year old female, designated CM, was treated for over a year with Composition A delivered transmucosally three times per day. The patient's CD4+ T cell count was 240 prior to the commencement of treatment, and 550 after three months of continued treatment. One week after the commencement of treatment, the patient reported a sensation of fullness in the abdomen, at which time a physical examination revealed a firm, fixed lump of approximately 7 cm in the left illiac fossa. No sonogram or X-ray was performed. Approximately two months after the commencement of treatment, the mass had regressed to about 3 cm, and after 9 months of treatment the mass was not detectable.

EXAMPLE 4
Reduction of the Symptoms of Feline Immunodeficiency Virus (FIV)

A ten year old stray cat testing positive for FIV was treated by a veterinarian with a composition of the invention to determine whether the composition was effective against this virus. The animal was FeLV negative. One cc doses of Composition A prepared as in the previous examples were injected once per day intravenously for 8 days, after which the doses were switched to intramuscular injection for twenty-one days. After this initial dose regimen, the animal tested weakly positive for FIV using a combination FIV Ab/FeLV Ag test kit (Idexx Corp., Portland, Me.). Dosages were increased to 4 cc IM for three days, then intravenously for 15 days, after which the FIV test was positive. Treatment was reduced to 1 cc IV per day for one month, and was discontinued because the animal was not eating. The animal's appetite and demeanor improved within three days of the cessation of treatment. Treatment with 0.5 cc IV once a day was re-started 6 weeks later for a duration of one month, followed by a week without treatment before daily IV doses of 1 cc for three weeks, after which treatment was discontinued. The animal remained in visible good healthfor three more years after the treatments ceased. Thirty one months after the cessation of treatment, and again 9 months after that, complete blood counts did not reveal the luekopenia indicative of active FIV, nor had there been a history of opportunistic infections that one would expect if the virus were active. The animal was euthanized forty months after the cessation of treatment, due to a primary pulmonary adenocarcinoma. It is believed, since blood work never revealed the blood cell changes that are indicative of the disease, that the treatments with the composition of the invention were effective in preventing the active stages of FIV disease.

EXAMPLE 5
Reduction in Tumor Size Following Treatment with a Composition of the Invention Composition A was administered at a dose of 1 gram via the oral transmucosal route three times a day to an individual with a palpable abdominal mass of approximately 7 cm in size. The individual was being treated primarily for the symptoms of active AIDS. However, over the course of treatment for three months, the solid tumor mass regressed to the point that it was no longer palpable.

Another $HIV^+$ patient with a palpable tumor mass (about 2 cm) in her breast was treated 3 times daily with 1 gram oral transmucosal doses of Composition A. Over the course of treatment for three months, the tumor mass regressed to the point where it was no longer palpable.

Another $HIV^+$ patient with two lung tumors, one approximately 5 cm×7.5 cm and another approximately 5 cm×2.5 cm, was treated 3 times daily with 1 gram oral transmucosal doses of Composition A. After three months of treatment, the tumors had both regressed or shrunken by approximately 50%. Treatment in this and several other patients being treated for active HIV, with or without accompanying tumors, was discontinued due to violent political unrest and an embargo of Haiti that made continued shipment of drugs and follow-up care impossible.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of increasing the number of $CD4^+$ T cells in an individual infected with human immunodeficiency virus, said method comprising the step of administering a therapeutically effective amount of a composition comprising the chemical compound having a structure selected from the group consisting of structures 1–4, such that said number of $CD4^+$ T cells is increased.

2. The method of claim 1 in which said composition is administered transmucosally.

3. The method of claim 1 in which said composition is administered parenterally.

4. A kit for performing the method of claim 1, said kit comprising a composition comprising the chemical compound having a structure selected from the group consisting of structures 1–4.

5. A method of maintaining the number of CD4+ T cells in an individual infected with human immunodeficiency virus, said method comprising the step of administering a therapeutically effective amount of a composition comprising the chemical compound having a structure selected from the group consisting of structures 1–4, such that said number of $CD4^+$ T cells is maintained.

6. The method of claim 5 in which said composition is administered transmucosally.

7. The method of claim 5 in which said composition is administered parenterally.

8. A kit for performing the method of claim 5, said kit comprising a composition comprising the chemical compound having a structure selected from the group consisting of structures 1–4.

* * * * *